(12) United States Patent
Yellepeddi

(10) Patent No.: US 7,430,273 B2
(45) Date of Patent: Sep. 30, 2008

(54) INSTRUMENT HAVING X-RAY FLUORESCENCE AND SPARK EMISSION SPECTROSCOPY ANALYSIS CAPABILITIES

(75) Inventor: Ravisekhar Yellepeddi, Chavornay (CH)

(73) Assignee: Thermo Fisher Scientific Inc., Waltham, MA (US)

( * ) Notice: Subject to any disclaimer, the term of this patent is extended or adjusted under 35 U.S.C. 154(b) by 0 days.

(21) Appl. No.: 11/710,153

(22) Filed: Feb. 23, 2007

(65) Prior Publication Data

US 2008/0205593 A1 Aug. 28, 2008

(51) Int. Cl.
*G01N 23/223* (2006.01)
(52) U.S. Cl. .......................................... 378/44; 378/45
(58) Field of Classification Search ............... 378/44–50
See application file for complete search history.

(56) References Cited

U.S. PATENT DOCUMENTS

| 4,592,655 | A | 6/1986 | Slickers ...................... 356/313 |
| 5,406,608 | A | 4/1995 | Yellepeddi et al. ............ 378/46 |
| 6,765,986 | B2 | 7/2004 | Grodzins et al. .............. 378/46 |
| 6,801,595 | B2 * | 10/2004 | Grodzins et al. .............. 378/45 |

FOREIGN PATENT DOCUMENTS

EP 1724570 A1 11/2006

\* cited by examiner

*Primary Examiner*—Thomas Courtney
(74) *Attorney, Agent, or Firm*—Charles B. Katz

(57) ABSTRACT

An analytical instrument is disclosed having both XRF and spark emission spectroscopy capabilities. In a particularly advantageous embodiment, a field portable XRF device is removably coupled to the instrument by means of a docking station. A first surface of the sample is irradiated with an X-ray beam, and the X-ray radiation fluorescently emitted from the sample is detected and analyzed to acquire elemental composition data. The instrument is further provided with a spark source located proximal a second surface of the sample and a detector for sensing the radiation emitted from the spark-excited material. The combined instrument enables the acquisition of complementary elemental composition data by XRF and spark emission spectroscopy without having to transport a sample between separate instruments.

19 Claims, 2 Drawing Sheets

INSTRUMENT HAVING X-RAY FLUORESCENCE AND SPARK EMISSION SPECTROSCOPY ANALYSIS CAPABILITIES

FIELD OF THE INVENTION

The present invention relates generally to analytical instruments for measurement of the elemental composition of materials, and more particularly to instruments for X-ray fluorescence and spark emission spectroscopy analysis.

BACKGROUND OF THE INVENTION

X-ray fluorescence (XRF) is a well known technology for analysis of the elemental composition of solid materials. In XRF, a focused X-ray beam is directed onto the surface of a sample. Atoms in the sample responsively emit X-ray photons having characteristic energies. One or more X-ray detectors are used to collect and convert the X-rays emitted by the sample into electronic signals that may be processed to determine the energy and number emitted of X-rays, which in turn provides information regarding the abundance of elements in the sample. XRF analyzers are commercially available in both laboratory (stationary) and portable forms. Field portable XRF analyzers situate the X-ray source, detector and related electronics within a handheld housing, and may be easily transported between inspection stations in an industrial manufacturing or processing facility or to the field for in situ analysis.

Because the sensitivity of XRF decreases with decreasing proton number (Z), XRF devices are generally not capable of quantitative analysis of light elements in the sample. For example, portable XRF instruments operating under air (i.e., without purging or evacuation of the region between the analyzer head and the sample) are typically limited to measurement of titanium and heavier elements ($Z \geq 22$). For this reason, XRF is often used in connection with other analysis techniques that yield information regarding the concentration of lighter elements, such as carbon, nitrogen, oxygen, phosphorous and sulfur. One such technique is spark emission spectroscopy, where a spark or arc (these terms are used interchangeably herein to denote an electrical discharge) is generated between an electrode positioned near the sample surface and the sample (or an electrode in contact with the sample) to vaporize and excite atoms of the sample. The excited atoms emit light of characteristic wavelength, which is detected and analyzed to measure elemental composition.

In common laboratory and industrial practice, a sample of a test material is analyzed serially in separate XRF and spark emission spectroscopy instruments. This practice requires the sample to be transported between the instruments, either manually or via a robotic apparatus, which increases the possibility of sample contamination and extends the analysis cycle time. Furthermore, sample surfaces may need to be prepared to different specifications for XRF and spark emission spectroscopy analyses, particularly when laboratory XRF instruments are utilized, necessitating separate sample preparation tools and procedures for the two instruments.

U.S. Pat. No. 6,801,595 ("X-ray Fluorescence Combined With Laser Induced Photon Spectroscopy" to Grodzins et al.) discloses an analytical instrument that integrates an XRF device with a laser induced photon fluorescence (LIPF) spectroscopy system. An X-ray source and a laser are arranged to irradiate overlapping regions of a sample surface, such that measurement data is obtained on the same sample volume. Among the purported advantages of conducting XRF and LIPF of the same sample volume is that the XRF data may be used to normalize LIPF data so that relative results acquired by LIPF may be made absolute. Although a device architecture of this type (whereby XRF and optical emission spectroscopy data are acquired for a common sample volume) may provide certain advantages in connection with the LIPF technique, it is not well-suited for use with spark emission spectroscopy.

SUMMARY

Roughly described, an analytical instrument constructed according to one embodiment of the present invention includes a platform for supporting thereon a sample to be analyzed, an X-ray source positioned to irradiate the first surface of the sample with an X-ray beam, and at least one X-ray detector arranged to detect X-rays fluorescently emitted by the sample in response to irradiation with the X-ray beam. The instrument is further provided with an electrode positioned near a second surface of the sample, the second surface being oriented in a direction different than and preferably opposite to that of the first surface. A voltage is applied to the electrode to generate a spark that vaporizes and excites a portion of the sample. The excited atoms emit light of characteristic wavelengths that is detected by at least one appropriately positioned emission sensor. By performing XRF and spark emission spectroscopy analyses on different surfaces of the sample, the analyses may be performed concurrently and without removing the sample from or repositioning the sample in the instrument.

In a particularly favorable implementation, the X-ray source and detector(s) are contained in a portable handheld XRF analyzer, which is releasably coupled to the instrument by means of a docking station. The docking station may include one or more attachment features for reproducibly holding the XRF analyzer in a desired position relative to the sample surface. The XRF can then be easily and quickly removed from the instrument and transported to another location for in situ use, and then re-coupled to the instrument for combined XRF/spark emission spectroscopy analysis.

DETAILED DESCRIPTION OF EMBODIMENTS

Figure 1:
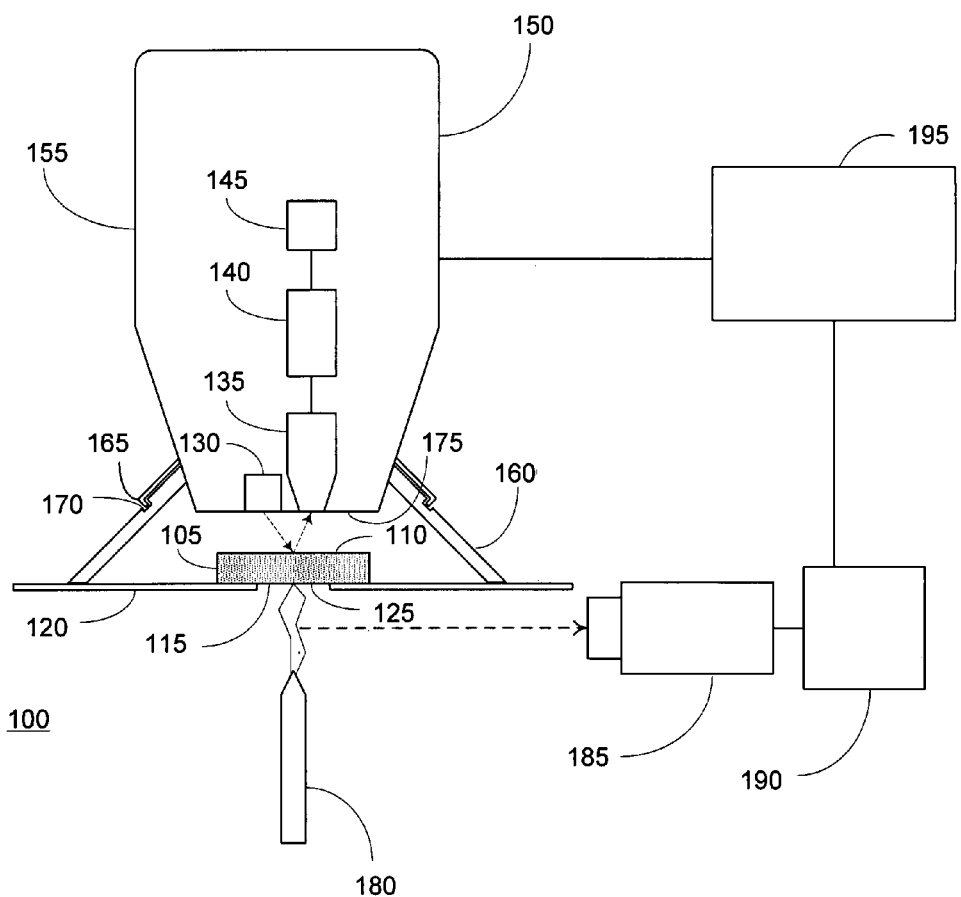
FIG. 1 depicts in rough schematic view a combined XRF/spark emission spectroscopy analytical instrument, according to one embodiment of the invention.

FIG. 1 depicts the primary components of an analytical instrument 100 constructed in accordance with one embodiment of the invention. An analyte sample 105 having first and second generally planar surfaces 110 and 115 is supported on a platform 120, which is adapted with an aperture 125 to permit physical access to second surface 115 from the region beneath platform 120. Sample 105 is prepared such that first and second surfaces 110 and 115 are oriented in different and preferably opposite directions such that sample 105 may be concurrently analyzed by XRF and spark emission spectroscopy, as is described below. In one particular implementation, platform 120 may be translatable in the plane of second surface 115 so that spark emission spectroscopy data may be acquired for spatially separated regions on the surface and an "averaged" elemental composition may be determined. Horizontal translation of the platform and sample 105 relative to the XRF analyzer may also be employed to obtain a spatially resolved map of elemental composition by irradiating spaced-apart regions on first surface 110 and measuring the resulting emitted radiation for each region.

Instrument 100 is provided with an X-ray source 130 arranged to irradiate a region of first surface 110 with an X-ray beam. X-ray source 130 may take the form of an X-ray tube or a quantity of a radioisotope, such as $^{241}$Am. As is known in the XRF art, irradiation of the sample with X-rays causes a portion of the constituent atoms in the sample to fluorescently emit X-rays having energies unique to the emitting element. The fluorescently emitted X-rays are sensed by an X-ray detector 135, which is operable to generate signals representative of the energies and intensities of the X-ray radiation emitted from the sample. X-ray detector 135 may be implemented, in one example, as a silicon p-i-n detector. The output of X-ray detector 135 is conveyed to a processor 140 (which may comprise any one or combination of general purpose microprocessors, digital signal processors, and application-specific circuitry) which collects and processes the signals to construct an X-ray spectrum and to convert the X-ray spectrum into elemental composition data. The calculated elemental data may be stored in internal memory 145 for later review and/or transfer to an external computer device.

In a particularly advantageous embodiment, X-ray source 130, detector 135, and processor 140 are contained within housing 150 of a field portable XRF device 155. Portable XRF device 155 may have a battery for powering the various components and a screen for displaying the determined elemental composition and other data to the user. Portable XRF device 155 may communicate with an external computer via a wireless or cable link for data transfer and to enable control of the device from the external computer. One example of a commercially available XRF device of this general description is the Niton XLt analyzer, manufactured and sold by Thermo Fisher Scientific (Waltham, Mass.). Detector 135 will typically be configured for energy-dispersive detection; alternatively, a wavelength-dispersive detection arrangement may be employed, which provides improved resolution and detection limits but is generally more expensive and bulkier relative to energy-dispersive detection.

XRF device 155 may be removably coupled to a docking station 160, which receives and holds a portion of the device housing and may additionally provide data, control power, cooling and purge/vacuum connections via one or more connectors (not depicted) that plug into corresponding connectors or ports located on XRF device 155. Docking station 160 may include a set of attachment features 165, such as clips, protrusions, detents, latches, grooves or pins, which releasably engage corresponding features 170 located on XRF device 155, such that the components of XRF device 155 (e.g., source 130 and detector 135) are reproducibly held at a desired position and orientation relative to first surface 110 when the device is coupled to docking station 160. Docking station 160 may be attached to platform 120 by a hinge arrangement to allow the docking station to be easily rotated away from platform for placement and removal of sample 105. In certain implementations, instrument 100 may be utilized for on-line analysis of samples in a sorting, processing or manufacturing environment. For such an implementation, an automated sample transport mechanism may be employed to move a sample to the appropriate position within instrument 100 for analysis by XRF device 155, and to remove the sample when the analysis has been completed so that another sample may be analyzed.

In one mode of operation of instrument 100, XRF device 155 is operated under air, meaning that the space between a face 175 of XRF device 155 and first surface 110 of sample 105 is filled with ambient air. As discussed above, an XRF device operated under air will typically be unable to measure elements lighter than titanium. If measurement of lighter elements is desired, the space between the XRF device face 175 and sample 105 may be purged with helium (which will typically extend measurement capabilities down to silicon) or evacuated (which will typically extend measurement capabilities down to boron) For this purpose, the lower margins of docking station 160 may sealingly engage sample 105 and/or the surrounding portions of platform 120, and the upper portions of docking station 160 may sealingly engage the corresponding surfaces of housing 150 to define a sealed region, and a port opening to the interior of the sealed region may be provided for connection to a vacuum pump or helium supply. In a particular implementation, XRF device face 175 may be removed such that the sealed region includes at least a portion of the interior volume of XRF device 155. Doing so enables the areas proximate to X-ray source 130 and detector 135 to be purged or evacuated, which allows measurements of lighter elements to be acquired with greater efficiency. Improvements in performance (detection of lighter elements and/or higher sensitivities) may also be achieved by use of better X-ray sources and wavelength-dispersive detection of the emitted fluorescent X-rays. However, doing so increases the complexity and cost of instrument 100 and possibly increases the analysis cycle time.

In accordance with another embodiment, docking station 160 may be omitted, and XRF device 155 may adapted with a plate that is positioned flush with the face of the device and extends radially outwardly therefrom. The plate is abutted to sample 105 during operation.

Instrument 100 further includes a spark electrode 180 having a terminal end positioned near second surface 115 of sample 105. A not-depicted DC or AC source supplies electrical power to the electrode to generate an electrical discharge (spark) between spark electrode 180 and sample 105. A ground electrode may be placed in electrical contact with sample 105 to complete the spark circuit, or the sample itself may serve as the ground electrode (via contact with grounded surfaces of platform 120). In order to achieve close control of the spark energy and thereby enable quantitative analysis, the region between spark electrode 180 may be flushed with argon or other inert gas. As is known in the spark emission spectroscopy art, the spark vaporizes a portion of sample 105 and excites atoms in the sample such that the atoms emit radiation of characteristic wavelengths. The emitted radiation is sensed by at least one appropriately positioned emission detector 185, which responsively generates signals representative of the wavelengths and intensities of the emitted light. These signals are then passed on to at least one processor 190 for construction of a spectrum and quantitative determination of elemental composition in accordance with well-established methods.

The XRF and spark emission spectroscopy subsystems may be independently controlled, or may alternatively communicate with and be under the common control of a computing device 190. The use of computing device 190 may be advantageous, as it allows the XRF and spark emission spectroscopy analysis cycles to be coordinated in an automated fashion, and further allows the two sets of elemental composition data (the set acquired by XRF and the set acquired by spark emission spectroscopy) to be joined so that the operator may easily inspect and review all of the elemental composition data available for a particular sample. Computing device 190 may take the form of an on-board data and control system integrated into a laboratory (i.e., fixed) spark emission spectroscopy system.

Figure 2:
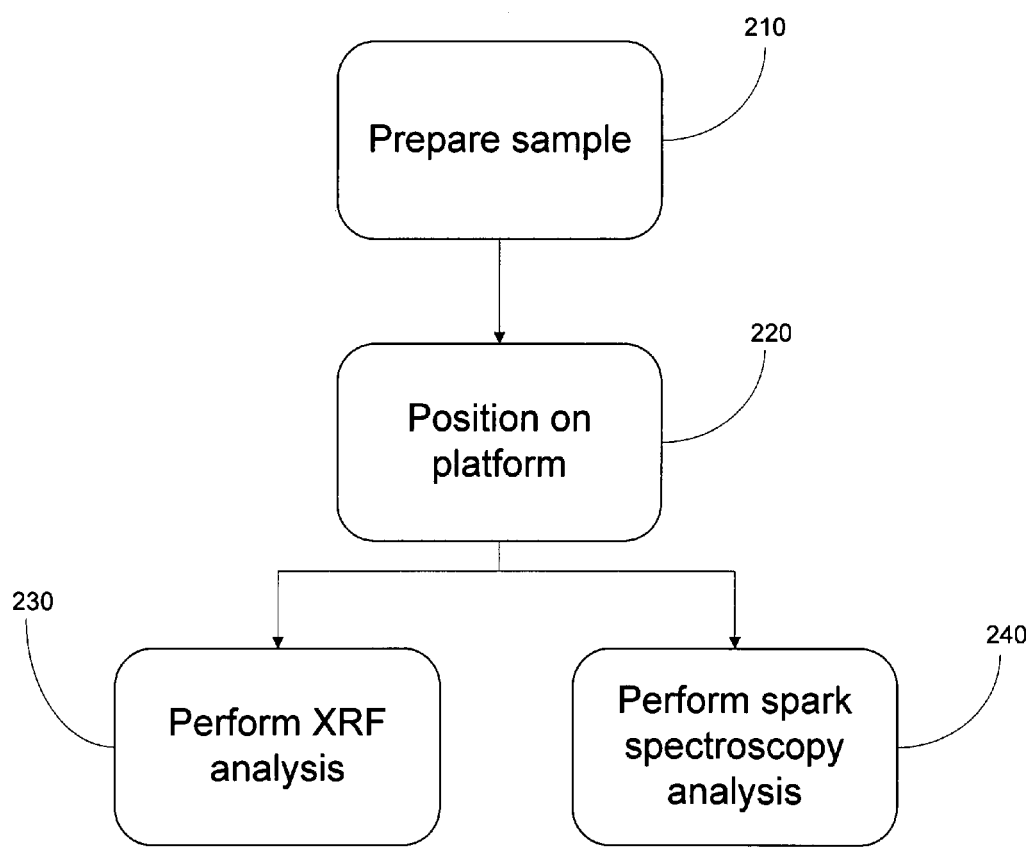
FIG. 2 is a flow diagram of a method for using the analytical instrument of FIG. 1.

FIG. 2 depicts the steps of a method for acquiring elemental composition information for a sample using the integrated XRF/spark emission spectroscopy instrument 100 described above. In the initial step 210, the sample is formed into a desired shape by cutting, molding or any other suitable operations. For instrument 100, the sample will optimally be formed as a thin disk having first and second major surfaces oriented in opposite directions, and a diameter sufficient to cover aperture 125 so that the gas compositions and pressures in the regions adjacent to the first and second surfaces may be controlled independently. The first and second surfaces are then finished to desired conditions (smoothness, absence of inclusions) by grinding and/or polishing. Generally, XRF analysis is less sensitive to surface conditions relative to spark emission spectroscopy (because the area irradiated is larger and because the X-ray beam penetrates the surface to a much greater distance), so the finishing requirements for XRF are less stringent. For this reason, the finishing specifications may be different for the first and second surfaces, e.g., first surface 110 may be prepared by grinding only, whereas second surface 115 may be prepared by grinding and polishing. Alternatively, both surfaces may be prepared to the more stringent finishing specifications required for spark emission spectroscopy. In another alternative, one surface of sample 105 is finished (e.g., by grinding and polishing) to spark emission spectroscopy specifications, and the other surface is left unfinished. For this alternative, the XRF and spark emission spectroscopy analysis cycles are performed sequentially—the finished surface is initially oriented toward XRF device 155 for XRF analysis, and subsequently turned over so that it is oriented toward spark electrode 180 for spark emission spectroscopy analysis.

Next, sample 105 is positioned on platform 120 within instrument 100, step 220. As discussed above, docking station 160 may be attached to platform 120 via a hinged arrangement, such that it may be easily swung away from platform 120 to permit access to the region in which the sample is placed. If a separate ground electrode is employed, the ground electrode may then be brought into contact with the sample.

Next, in step 230, XRF analysis of sample 105 is performed by operating XRF device 155 to irradiate first surface 110 and measure the energies and intensities of the fluorescently emitted X-ray photons. The XRF analysis cycle may be initiated manually by an operator or may instead be initiated under the control of computing device 190. As is known in the art, the recorded fluorescent X-ray spectrum may be converted (using known reference data relating to characteristic X-ray energies) to elemental composition data representing the concentration of minor and major elemental components of the sample. As noted above, composition data for low-Z elements (e.g., elements lighter than titanium for a portable XRF device operating under air) will not be measured by XRF analysis. The typical analysis cycle time for a portable XRF device will be about 5-10 seconds.

Finally, in step 240, spark emission spectroscopy analysis of sample 105 is conducted by generating an electrical discharge between spark electrode 180 and second surface 115, and measuring the wavelengths and intensities of the light emitted from the excited atoms. This spectrum is then converted to elemental composition data. In some implementations, a plurality of spectra may be acquired by serially exposing different areas of second surface 115 to the electrical discharge (e.g., by moving the sample and/or the spark electrode), and an averaged elemental composition may be calculated from the plural spectra in order to reduce noise or an anomalous results arising from surface inclusions. If spatially resolved XRF measurements are desired, then different areas of first surface 110 may be irradiated with the X-ray beam and the resultant fluorescently emitted X-rays detected while the plural optical emission spectra are acquired. Generally, the elemental composition data derived from the spark spectroscopy measurements will include information on relatively low-Z elements (e.g., carbon, nitrogen and oxygen) that are not measured by XRF analysis. The typical time required to complete the spark emission spectroscopy analysis is 30-45 seconds (which analysis time is commensurate, within a factor of two or so, with that of an XRF measurement). Preferably, the XRF (step 230) and spark emission spectroscopy analyses (step 240) are performed concurrently (as depicted in FIG. 2) to minimize the total analysis time, although some implementations (for example, where only one surface of the sample is prepared, as described above) may require the analyses to be performed sequentially.

It should be noted that the arrangement of FIG. 1 is especially well suited to simultaneous XRF/OES inspection since the surface 120 and the conducting sample 115 can form one side of an electrically isolated Faraday Cage, that effectively minimizes the EMI radiation from the spark, allowing the concurrent operation of the XRF.

Although the invention has been described with reference to a spark emission spectroscopy system, other embodiments may utilize excitation sources other than a conventional spark or arc to excite atoms at or near the second surface such that they emit light of characteristic wavelengths. In one illustrative example, a laser induced photon spectroscopy (LIPS) technique may be utilized in place of spark emission spectroscopy. The LIPS (also referred to as laser-induced breakdown spectroscopy, or LIBS) technique is well-known in the spectroscopy art and hence need not be described herein. In a LIPS-based embodiment of the present invention, a laser source is positioned to direct a radiation beam of suitable wavelength and power onto an area on second surface 115 of sample 105. The impingement of the laser beam unto the sample surface produces a plasma that excites atoms and the sample and causes them to fluorescently emit optical and near ultra-light of characteristic wavelengths. This light is sensed by at least one appropriately positioned emission detector, which responsively generates signals representative of the wavelengths and intensities of the emitted light. In a manner similar to operation of a spark emission spectroscopy-based analyzer, the signals generated by the detector are conveyed to a processor for construction of a spectrum and quantitative determination of elemental composition in accordance with well-established methods.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An analytical instrument, comprising:
   a platform for supporting a sample having first and second surfaces oriented in opposite directions;
   an X-ray source positioned to irradiate the first surface of the sample with an X-ray beam;
   at least one X-ray detector arranged to detect X-rays fluorescently emitted by the sample in response to irradiation with the X-ray beam;
   a spark electrode positioned adjacent to the second surface and having a voltage controllably applied thereto to generate a discharge at or proximate to the second surface to excite atoms in the sample, and at least one emission detector arranged to detect light emitted by the excited atoms.

2. The analytical instrument of claim 1, wherein the X-ray source and the at least one X-ray detector are contained within a housing of a portable X-ray fluorescence analyzer device removably coupled to a docking station.

3. The analytical instrument of claim 1, wherein the docking station has one or more attachment features for releasably engaging corresponding features on the housing of the analyzer.

4. The analytical instrument of claim 2, wherein the interior volume of the docking station defines a sealed region between the X-ray fluorescence analyzer device and the sample.

5. The analytical instrument of claim 2, wherein the sealed region extends at least partially into a volume interiorly defined by the analyzer housing.

6. The analytical instrument of claim 4, wherein the docking station includes a port communicating with a gas source or pump for respectively purging or evacuating the sealed region.

7. The analytical instrument of claim 1, wherein the spark electrode is disposed within a chamber flushed with argon gas.

8. The analytical instrument of claim 1, further comprising a common computing device for coordinating the XRF and spark emission spectroscopy analyses of the sample.

9. A method of analyzing a sample having first and second surfaces directed in opposite directions, comprising:
  (a) irradiating the first surface with an X-ray beam;
  (b) detecting X-rays fluorescently emitted by the sample in response to irradiation with the X-ray beam;
  (c) generating an electrical discharge at or proximate to the second surface, and detecting light responsively emitted by excited atoms of the sample.

10. The method of claim 9, further comprising a step of determining a first set of elemental composition data from the detected fluorescent X-rays, and a second set of elemental composition data from the emitted light.

11. The method of claim 9, wherein steps (a), (b) and (c) overlap in time.

12. The method of claim 9, further comprising a step of evacuating or flushing with helium a region adjacent to the first surface of the sample.

13. The method of claim 9, further comprising a step of flushing with argon a region adjacent to the second surface of the sample.

14. A spark emission spectrometer, comprising:
  a platform for supporting a sample having first and second surfaces oriented in opposite directions;
  a spark electrode positioned adjacent to the second surface and having a voltage controllably applied thereto to generate a discharge at or proximate to the second surface to excite atoms in the sample;
  at least one emission detector arranged to detect light emitted by the excited atoms; and
  a docking station configured to receive and hold a housing of a portable X-ray fluorescence analyzer device such that the device irradiates and detects X-rays fluorescently emitted from a first surface of the sample.

15. The analytical device of claim 1, wherein the X-ray detector is configured for energy-dispersive detection.

16. The analytical device of claim 1, wherein the X-ray detector is configured for wavelength-dispersive detection.

17. An analytical instrument, comprising:
  a platform for supporting a sample having first and second surfaces oriented in opposite directions;
  an X-ray source positioned to irradiate the first surface of the sample with an X-ray beam;
  at least one X-ray detector arranged to detect X-rays fluorescently emitted by the sample in response to irradiation with the X-ray beam;
  an excitation source configured to cause atoms in the sample located at or adjacent to the second surface to become excited and emit light;
  at least one emission detector arranged to detect light emitted by the excited atoms.

18. The analytical instrument of claim 17, wherein the excitation source includes a spark electrode.

19. The analytical instrument of claim 17, wherein the excitation source is includes a laser.

* * * * *

UNITED STATES PATENT AND TRADEMARK OFFICE
CERTIFICATE OF CORRECTION

PATENT NO. : 7,430,273 B2
APPLICATION NO. : 11/710153
DATED : February 23, 2007
INVENTOR(S) : Yellepeddi et al.

It is certified that error appears in the above-identified patent and that said Letters Patent is hereby corrected as shown below:

On the Title page, Item (75) Inventor:
replace "Ravisekhar Yellepeddi, Chavornay (CH)"
with --Ravisekhar Yellepeddi, Chavornay (CH) and Lee Grodzins, Lexington (USA)--

Signed and Sealed this

Second Day of December, 2008

JON W. DUDAS
*Director of the United States Patent and Trademark Office*

UNITED STATES PATENT AND TRADEMARK OFFICE
CERTIFICATE OF CORRECTION

PATENT NO. : 7,430,273 B2 Page 1 of 1
APPLICATION NO. : 11/710153
DATED : September 30, 2008
INVENTOR(S) : Yellepeddi et al.

It is certified that error appears in the above-identified patent and that said Letters Patent is hereby corrected as shown below:

On the Title page, Item (75) Inventor:
replace "Ravisekhar Yellepeddi, Chavornay (CH)"
with --Ravisekhar Yellepeddi, Chavornay (CH) and Lee Grodzins, Lexington (USA)--

This certificate supersedes the Certificate of Correction issued December 2, 2008.

Signed and Sealed this

Thirtieth Day of December, 2008

JON W. DUDAS
*Director of the United States Patent and Trademark Office*